(12) United States Patent
Zeng et al.

(10) Patent No.: US 9,225,915 B2
(45) Date of Patent: Dec. 29, 2015

(54) CALIBRATION AND QUANTIFICATION METHOD FOR GAS IMAGING CAMERA

(71) Applicant: Providence Photonics, LLC, Baton Rouge, LA (US)

(72) Inventors: Yousheng Zeng, Baton Rouge, LA (US); Jon Morris, Baton Rouge, LA (US)

(73) Assignee: PROVIDENCE PHOTONICS, LLC, Baton Rouge, LA (US)

( * ) Notice: Subject to any disclaimer, the term of this patent is extended or adjusted under 35 U.S.C. 154(b) by 19 days.

(21) Appl. No.: 13/935,988

(22) Filed: Jul. 5, 2013

(65) Prior Publication Data

US 2014/0008526 A1 Jan. 9, 2014

Related U.S. Application Data

(60) Provisional application No. 61/668,781, filed on Jul. 6, 2012.

(51) Int. Cl.
| | |
|---|---|
| H04N 5/33 | (2006.01) |
| G01N 21/3504 | (2014.01) |
| G01N 21/27 | (2006.01) |
| G01J 5/00 | (2006.01) |
| G01J 5/52 | (2006.01) |
| G01M 3/00 | (2006.01) |
| G01M 3/38 | (2006.01) |

(52) U.S. Cl.
CPC ............... *H04N 5/33* (2013.01); *G01J 5/0014* (2013.01); *G01J 5/522* (2013.01); *G01M 3/007* (2013.01); *G01M 3/38* (2013.01); *G01N 21/274* (2013.01); *G01N 21/3504* (2013.01); *G01J 2005/0048* (2013.01); *G01J 2005/0077* (2013.01); *G01N 2021/3513* (2013.01)

(58) Field of Classification Search
CPC .............. G01N 21/3504; G01N 21/00; G01N 33/0004; H04N 5/33; H04N 5/332
USPC ........................................................ 250/338.5
See application file for complete search history.

(56) References Cited

U.S. PATENT DOCUMENTS

| | | | |
|---|---|---|---|
| 5,430,293 A * | 7/1995 | Sato et al. ..................... 250/330 |
| 8,653,461 B1 * | 2/2014 | Benson et al. ............. 250/339.01 |
| 2008/0231719 A1* | 9/2008 | Benson et al. ............. 348/222.1 |
| 2010/0064777 A1* | 3/2010 | Howieson ..................... 73/40.7 |
| 2013/0289899 A1* | 10/2013 | Tolton et al. .................... 702/51 |

* cited by examiner

*Primary Examiner* — Marcus Taningco
(74) *Attorney, Agent, or Firm* — Robert E. Bushnell, Esq.

(57) ABSTRACT

The calibration/verification system and method for gas imaging infrared cameras standardizes the procedures to objectively and consistently check performance of gas imaging infrared cameras. This system includes a background board maintaining a uniform temperature, a target cell filled with a target compound and disposed in front of the background board, a reference cell filled with a reference compound and disposed in front of the background board, and an analyzer coupled to the camera that captures images of the gas cell and the reference cell. The analyzer compares the intensity difference and the temperature difference of rays passing through the target cell and reference cell to a reference relationship data of a quality control chart to determine whether the camera is in a working condition. The method is further extended to provide a quantitative measurement of a hydrocarbon plume from a gas imaging infrared camera.

19 Claims, 7 Drawing Sheets

FIG. 6 ary measurement
of concentration and/or leak rate using gas imaging cameras.

CALIBRATION AND QUANTIFICATION METHOD FOR GAS IMAGING CAMERA

CLAIM OF PRIORITY

This application claims priority under 35 U.S.C. §119 to Provisional Patent Application No. 61/668,781, entitled "CALIBRATION/VERIFICATION DEVICE FOR GAS IMAGING INFRARED CAMERAS" filed on the 6 Jul. 2012, which application is incorporated herein by reference.

BACKGROUND OF THE INVENTION

1. Field of the Invention

The present invention relates to a calibration and quantification method for gas imaging infrared (IR) cameras. The calibration and/or verification system and method quantitatively determine the performance of a particular gas imaging IR camera, and determine whether the gas imaging IR camera is in a working condition. The quantification method determines the concentration and/or leak rate observed by a gas imaging IR camera.

2. Description of the Related Art

In recent years, gas imaging Infrared (IR) cameras have become a popular tool in hydrocarbon processing industries for gas leak detection. On Dec. 22, 2008, the U.S. Environmental Protection Agency (EPA) promulgated the Alternative Work Practice (AWP) rule (40 CFR §60.18, §63.11, and §65.7) that allowed regulated facilities to use IR cameras to detect leaks for compliance with the Federal Leak Detection and Repair (LDAR) regulations. On Mar. 26, 2012, EPA proposed a Uniform Standards (40 CFR 65) that also included IR camera for equipment leak detection. Compared to the conventional method of checking equipment leak component by component using a portable flame ionization detector (FID) per 40 CFR 60 Appendix A-7, Method 21, the IR camera method can check a large number of components in the field of view at once, and therefore it is less labor intensive. It can also be used for inspection of components that are difficult to reach with conventional methods.

For regulatory applications, the operators of the IR camera are required to perform a daily camera check per 40 CFR §60.18 (i)(2). The daily check is qualitative meaning in which the operator will either "see" gas or not "see" gas. Many factors affect the camera's ability to "see" gas, such as the type of background, temperature, sunlight, camera's condition, operator's experience in interpreting IR imagery, etc. There is no standard across different facilities by which a camera can be deemed to be in good working condition. The gas imaging IR cameras require sophisticated filters and cooled detectors. A slight difference in the performance of the cooling system or the narrow bandpass filter could significantly change the sensitivity of the camera to particular compounds. The qualitative and subjective daily check that is currently performed would unlikely detect the change in sensitivity of one camera or sensitivity difference among different cameras. Accordingly, a method and system to quantitatively determine the performance of a particular gas imaging IR camera are needed.

A limiting factor for the adoption of gas imaging technology as a complete replacement for conventional methods of leak detection is the inability to provide a quantitative measurement. While gas imaging cameras have been accepted as an approved AWP, the rule still requires inspection by conventional methods at least one quarter per year. Accordingly, a method is needed to determine a quantitative measurement of concentration and/or leak rate using gas imaging cameras.

SUMMARY OF THE INVENTION

The calibration/verification system for gas imaging infrared cameras described in this specification is designed to establish metrics and standardize the procedures to objectively and consistently check performance of gas imaging IR cameras.

The verification system includes a background board maintaining a uniform temperature, a target cell filled with a target compound and disposed in front of the background board, a reference cell filled with a reference compound and disposed in front of the background board, and an analyzer coupled to the camera that captures images of the gas cell and the reference cell. The analyzer includes a machine readable storage medium that provides instructions that cause a machine apparatus to perform operations to verify the camera. The operation includes steps of detecting an average intensity of rays passing through the target cell, detecting an average intensity of rays passing through the reference cell, acquiring an intensity difference between the average intensity of rays passing through the target cell and the average intensity of rays passing through the reference cell, and acquiring a temperature difference between a temperature of the background board and a temperature of the target cell.

The verification system may further include a temperature controller coupled to the background board to uniformly maintain the temperature of the background board. The verification system may further include a background board temperature sensor to detect the temperature of the background board, and a cell temperature and pressure sensor to detect the temperature of the target cell.

The reference compound may include nitrogen gas or another gas that does not have a absorption band in the spectral bandpass of the IR camera, and the target compound may include a mixture of a hydrocarbon compound (e.g., ethylene, or benzene) and nitrogen.

The target cell may have a front window facing the camera, and a rear window facing the background board. The front and rear windows of the target cell are made of an infrared transparent material. The reference cell may have a front window facing the camera, and a rear window facing the background board. The front and rear windows of the reference cell are made of the same infrared transparent material as in the target cell.

The target cell and the reference cell are disposed in front of the background board maintaining the same distances from the background board.

The analyzer may include a quality control chart including a reference relationship data that includes a relationship between an intensity difference data and a temperature difference data of the target compound.

The operation of the machine readable storage medium may further include steps of comparing the intensity difference and the temperature difference to the reference relationship data of the quality control chart, and determining whether the camera is in acceptable working condition.

Another aspect of the present invention provides a method to verify a camera. The method includes steps of maintaining a uniform temperature of a background board, detecting an average intensity of rays passing through a target cell that is filled with a target compound and disposed in front of the background board, detecting an average intensity of rays passing through a reference cell that is filled with a reference compound and disposed in front of the background board, acquiring an intensity difference between the average intensity of rays passing through the target cell and the average intensity of rays passing through the reference cell, acquiring a temperature difference between a temperature of the background board and a temperature of the target cell, and comparing the intensity difference and the temperature difference to a reference relationship data of a quality control chart. The reference relationship data includes a relationship between an intensity difference data and a temperature difference data of the target compound.

Another aspect of the present invention extends the relationship between intensity difference and temperature difference in an infrared image to quantify the path concentration of a hydrocarbon plume. The path concentration is the product of hydrocarbon concentration and plume path length, and may be measured as parts per million-meter (ppm-m). If the plume path length is given or can be measured, the concentration can be calculated by dividing the path concentration by path length. The method includes steps of determining the boundary of a hydrocarbon plume in an infrared image, detecting an average intensity of rays passing through and attenuated by the hydrocarbon plume for each pixel within the boundary of the plume, detecting an average intensity of rays passing through and not attenuated by the hydrocarbon plume for each pixel within the boundary of the plume, detecting the temperature of the background for each pixel within the boundary of the plume, detecting the temperature of the hydrocarbon plume for each pixel within the boundary of the plume, acquiring an intensity difference between the average intensity of rays passing through and attenuated by the plume and the average intensity of rays passing through and not attenuated by the hydrocarbon plume, acquiring a temperature difference between the hydrocarbon plume and the background, and using the pre-established intensity difference and temperature difference chart to determine the path concentration of the hydrocarbon plume in ppm-m (or another "concentration-path length" unit). The method further detects features in the hydrocarbon plume which can be used to determine the speed and the size of the plume, which in turn can be used to calculate flux for a specified region of interest. The method further determines the leak rate based on the flux and converts it into a mass leak rate such as pounds per hour.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

The present invention will now be described more completely with reference to the accompanying drawings, in which exemplary embodiments of the invention are shown.

Figure 1A:
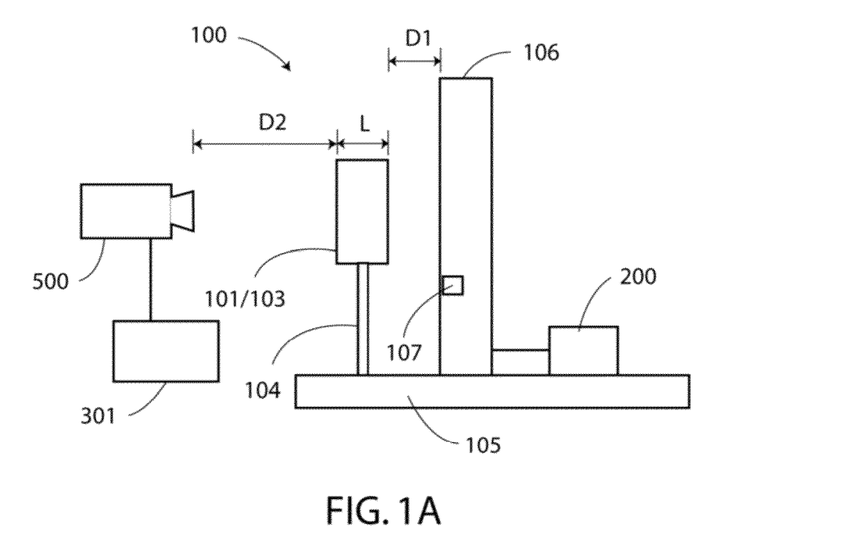
FIG. 1A shows a calibration/verification system for gas imaging infrared cameras in a side view.
Figure 1B:
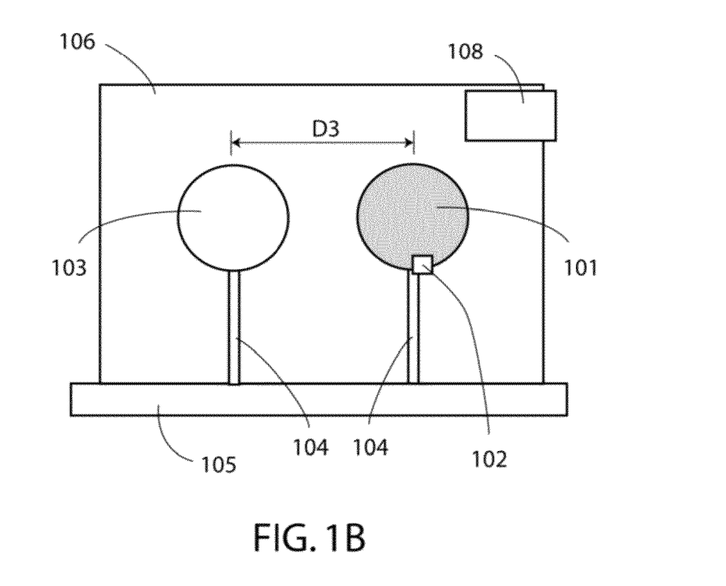
FIG. 1B shows the calibration/verification system for gas imaging infrared cameras in a front view.

The verification system 100 for validating or calibrating the performance of a gas imaging infrared (IR) camera is illustrated in FIGS. 1A and 1B. The side view of the verification system 100 is shown in FIG. 1A, and a front view of the verification system 100, viewed from the position of a camera 500, is shown in FIG. 1B. The camera 500 is a gas imaging IR camera to be verified or calibrated. The camera 500 includes any imaging system that is capable of detecting gas leak. The camera 500 may be an infrared imaging system, but is not limited to this type of imaging system.

Referring to FIGS. 1A and 1B, the verification system 100 includes two gas-filled cells 101 and 103, a background board 106, a temperature controlling unit 200 that controls temperature of the background board 106, and a pixel intensity analyzer (PIA) 301 that is connected to the camera 500 to be verified or calibrated.

The target cell 101 is filled with a target hydrocarbon compound and nitrogen (or an inert reference gas) at a given ratio, i.e., the concentration of the hydrocarbon is fixed and known. The reference gas may include oxygen or other gas that does not have a strong absorbance spectral feature. The gas mixture is sealed inside the cell maintaining a slightly higher pressure than atmosphere. For example, if the target compound is benzene, the target cell 101 may be filled with 10% of benzene and 90% of nitrogen. The reference cell 103 is filled with a reference compound, which is nitrogen gas in an embodiment. These two cells are metal cylinders with front and rear windows made with an infrared (IR) transparent material (e.g., fused silica). The front windows of the cells 101 and 103 may face the camera 500, and the rear windows of the cells 101 and 103 may face the background board 106.

The verification system 100 may further include a background board temperature sensor 107 to detect the temperature of the background board 106, and a cell temperature and pressure sensor 102 that detects temperature and pressure of the target cell 101.

A front face of the background board 106, which faces the target cell 101 and the reference cell 103, is painted black and has matte texture to minimize reflection of IR rays from the surrounding environment. The background board 106 is coupled to a temperature controlling unit 200 to maintain a constant temperature and to uniformly distribute the constant temperature over the background board 106.

Figure 1C:
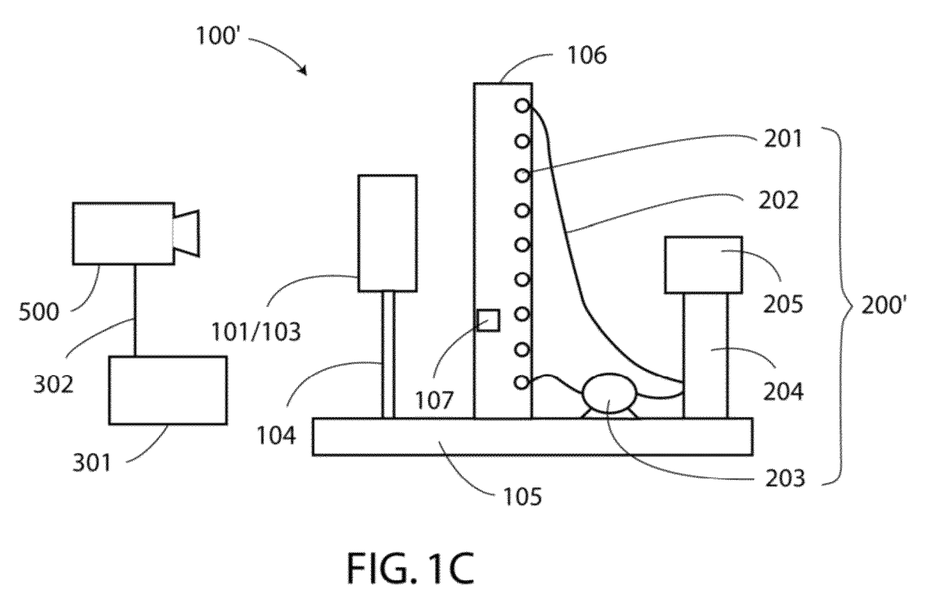
FIG. 1C shows a side view of a calibration/verification system for gas imaging infrared cameras constructed as one embodiment of the present invention.

In one embodiment of the verification system 100', the temperature controlled background board 106 achieves a uniform temperature distribution by circulating water through a thick aluminum sheet. FIG. 1C exemplarily shows the background board 106 coupled to a temperature controlling unit 200' that includes a water-circulating system. In the embodiment shown in FIG. 1C, the temperature controlling unit 200' includes a water reservoir 204, a temperature controller 205, a water recirculation pump 203, a water recirculation coil 201 that is installed in the background board 106, and a water supply tube 202 that connects the water circulation coil 201 to the water recirculation pump 203 and the water reservoir 204.

This structure allows the background board 106 to be uniformly heated or cooled with respect to the temperature of the two cells 101 and 103.

However, the temperature controlling unit 200 is not limited to the water circulating apparatus as shown in FIG. 1C. Any device or system that is capable of uniformly heating or cooling the background board 106 can be employed for the temperature controlling unit 200 of the verification system 100. Other embodiments may include a background board 106 that is thermoelectrically heated or cooled to achieve a uniform temperature. The cells 101 and 103 may be equilibrated to the ambient environmental temperature.

In the embodiment of the present invention as shown in FIGS. 1A and 1B, the target cell 101 and the reference cell 103 are placed on a base board 105 through cell holders 104. The target cell 101 and the reference cell 103 are spaced apart from each other by a distance D3, and are arranged parallel to the background board 106, maintaining a distance D1 from the background board 106. The camera 500 to be verified or calibrated is placed in front of the target cell 101 and the reference cell 103 maintaining a distance D2 from the cells.

The camera 500 takes images of both the target cell 101 and reference cell 103 simultaneously, and the images of the cells are transferred to the pixel intensity analyzer 301 for the analysis of the intensities coming from the target cell 101 and the reference cell 103. This analysis will quantitatively determine whether or not the camera 500 is in a good working condition.

The verification system 100 may further includes a display panel 108 that displays the temperature of the background board 106, which is measured by the background board temperature sensor 107, and the temperature of the target cell 103, which is measured by the cell temperature and pressure sensor 102. These temperatures of the background board 106 and the target cell 101 are input to the pixel intensity analyzer 301 together with the intensities of the images of the target and reference cells to verify the camera 500. The input of the temperatures of the background board 106 and the target cell 103 can be done manually or electronically. The pixel intensity analyzer 301 can be coupled to the background board temperature sensor 107 and the cell temperature and pressure sensor 102, and the temperatures of the background board 106 and the target cell 101 can be electronically transferred to the pixel intensity analyzer 301.

When the background board 106 reaches a uniform temperature (the temperature uniformity can be confirmed through the IR camera 500), the IR camera 500 is used to capture images of the front view of the background board 106 that includes the target cell 101 and the reference cell 103. In the image captured by the IR camera 500, the target cell 101, which includes a target compound, will have different pixel intensity from that of the reference cell 103, which includes nitrogen gas or a reference compound.

The difference in IR intensity is a function of the nature, concentration and pressure of the target gas contained in the target cell 101, the thickness L of the target cell 101, and the temperature differential ($\Delta T$) between the target cell 101 and the background board 106. For a given target cell, the nature, concentration and pressure of the target gas and the thickness of the cell is fixed. At a specified distance between this verification system 100 and the IR camera 500, the differential IR intensity ($\Delta I$) of the pixels representing the target cell and the reference cell is a function of the temperature difference ($\Delta T$). The relationship between $\Delta I$ and $\Delta T$ can be established.

For the specific set-up illustrated in FIGS. 1A and 1B, the IR signal coming into the IR camera can be described by the following simplified radiative transfer equation (RTE):

$$I = [\epsilon(\lambda)B(T_b, \lambda) - B(T_g, \lambda)]\exp^{[-\alpha(\lambda)CL]} + B(T_g, \lambda)$$

where I is IR energy intensity detected by the IR camera, $\lambda$ is a wavelength of IR ray, $\epsilon(\lambda)$ emissivity of the background board, which is a function of wavelength $\lambda$, $B(T_b, \lambda)$ is Planck function for the background board, which is a function of $\lambda$ and temperature $T_b$ of the background board, $B(T_g, \lambda)$ is Planck function for the target cell, which is a function of $\lambda$ and temperature Tg of the target cell, $\alpha(\lambda)$ is an absorption coefficient of the gas in the target cell, which is a function of $\lambda$, C is a concentration of the gas in the target cell, and L is the thickness of the target cell, i.e., the optical path length of the gas in the target cell.

If the pressure in target cell 101 is higher than the standard pressure, the concentration C should be adjusted proportionately to account for the increase in number of molecules that can absorb the IR energy. The Plank function can be expressed as below:

$$B(T, \lambda) = \frac{2hc^2}{\lambda^5} \frac{1}{e^{\frac{hc}{\lambda k_B T}} - 1}$$

where h is a Planck constant, c is a speed of light, and $K_B$ is a Boltzmann constant.

Figure 2:
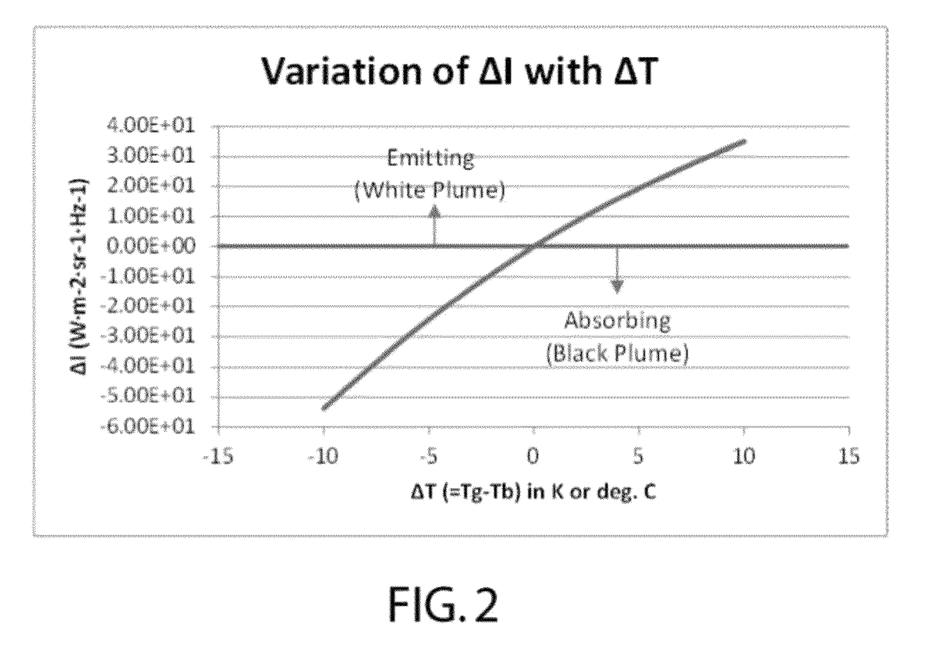
FIG. 2 shows a graph presenting the relationship between the temperature difference ΔT and the intensity difference ΔI.

At a specific value of wavelength $\lambda$ (for example, 3.2 μm), the emissivity of the background board (for example, $\epsilon=1$), gas absorption coefficient (for example, $\alpha=0.8$), the thickness of the target cell (for example, L=0.1 m), and gas concentration (for example, C=1.0%), the IR energy intensity I can be calculated for various temperature differences between the temperatures of the target cell 101 and the background board 106 (i.e. temperature difference $\Delta T = Tg - Tb$, where Tg is the temperature of the target cell and Tb is the temperature of the background board). The results of the intensity difference $\Delta I$ for various temperature differences $\Delta T$ are shown in FIG. 2 (the thicker line crossing a reference line of $\Delta I=0$). Herein, the intensity difference $\Delta I = I_{Gas} - I_{Ref}$, where $I_{Gas}$ is the intensity of the target cell (or target intensity) and $I_{Ref}$ is the intensity of the reference cell (or reference intensity).

Figure 3:
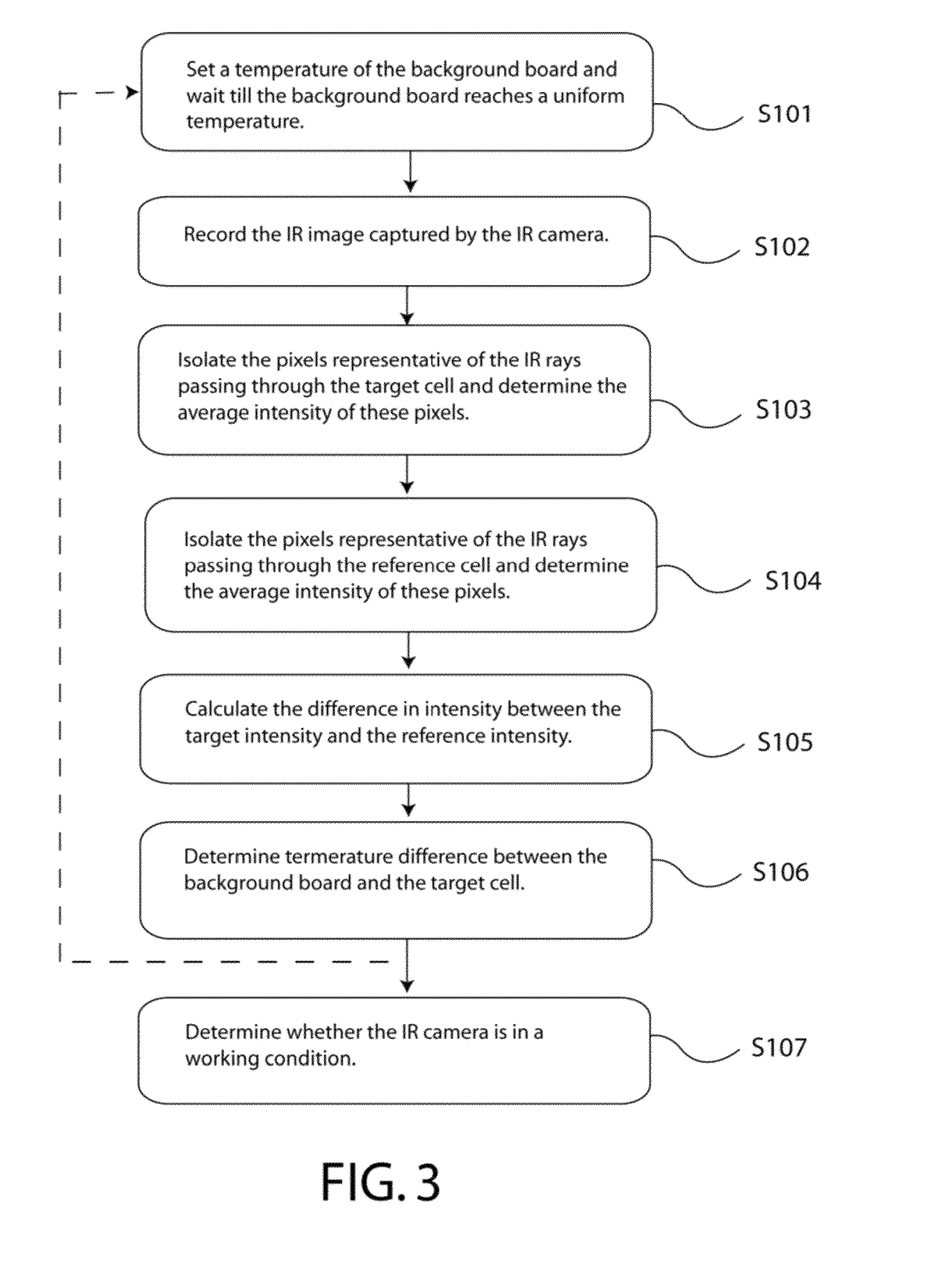
FIG. 3 shows a flowchart for performing the calibration or verification of a gas imaging infrared camera.

The pixel intensity analyzer (PIA) 301 is connected to the camera 500 to be verified or calibrated. Once an image of the target cell 101 and the reference cell 103 is taken by the IR camera 500, the image data is transferred to the pixel intensity analyzer 301 from the IR camera 500. The pixel intensity analyzer 301 includes a machine readable storage medium that provides instructions that cause a machine apparatus to perform operations to verify or calibrate the IR camera 500. The machine readable storage medium include the data of intensity difference values $\Delta I$ for various temperature differences $\Delta T$, such as exemplarily shown in FIG. 2. The instruction of the machine readable medium of the pixel intensity analyzer 301 performs the following processes to verify the camera 500. FIG. 3 shows a flowchart that illustrates the camera verification processes.

Referring to FIG. 3, the background board 106 is set to a temperature and the verification process may start when the background board 106 reaches a uniform temperature over the background board (S101). Then, the pixel intensity analyzer 301 records the IR image captured by the IR camera 500, preferably in the raw 14-bit data format rather than the 8-bit data format processed for display on a monitor (S102). The pixel intensity analyzer 301 isolates the pixels representative of the IR rays passing through the target cell 101 and acquires the average intensity $I_{Gas}$ of these pixels of the target cell 101 (S103). The average intensity $I_{Gas}$ can be referred to as a target intensity. The intensity of these pixels is expected to be generally uniform within the isolated image of the target cell. Then, the pixel intensity analyzer 301 isolates the pixels representative of the IR rays passing through the reference cell 103 and acquires the average intensity $I_{Ref}$ of these pixels of the reference cell 103 (S104). The average intensity $I_{Ref}$ can be referred to as a reference intensity. The intensity of these pixels is expected to be generally uniform within the isolated image of the reference cell.

Then, the difference in intensity ($\Delta I = I_{Gas} - I_{Ref}$) between the target intensity $I_{Gas}$ and the reference intensity $I_{Ref}$ is calculated (S105). The reference intensity $I_{Ref}$ is used to represent the intensity of the background board ($I_b$) as it passes through the reference cell to the IR camera.

Subtracting the reference intensity $I_{Ref}$ from the target intensity $I_{Gas}$ allows system to cancel out potential bias to the measurement of the background board intensity $I_b$. The temperature difference $\Delta T = Tg - Tb$, where Tg is the temperature of the target cell and Tb is the temperature of the background board, is determined through the cell temperature and pressure sensor 102 and the background board temperature sensor 107 (S106). The processes through the steps 101 through 106 can be repeated to obtain the intensity difference $\Delta I$ for various temperatures of the background board 106.

Figure 4:
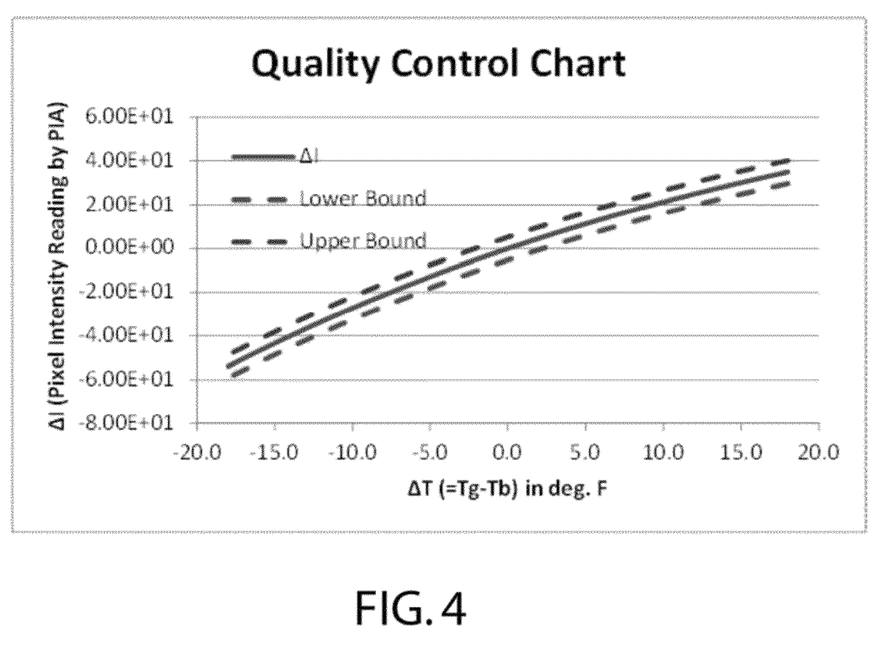
FIG. 4 shows a graph presenting quality control chart including an acceptable upper bound and acceptable lower bound curves to quantitatively determine the performance of a gas imaging IR camera.

With the above intensity difference $\Delta I$ acquired and calculated by the pixel intensity analyzer 301 and with the temperature difference $\Delta T$, the pixel intensity analyzer will plot the intensity difference $\Delta I$ as a point on a quality control (QC) chart (S107) for this IR camera under test. One example is shown in FIG. 4. The solid line in FIG. 4 represents the acquired and calculated intensity difference $\Delta I$ of the IR camera under test, as a function of the temperature difference $\Delta T$. The dashed lines represent upper bound and lower bound lines, which are saved in the pixel intensity analyzer 301 before testing the IR camera under test. Each of the upper bound and the lower bound is a reference relationship data that includes a relationship between intensity difference data and temperature difference data for the given target compound. The intensity difference of the reference relationship data can be drawn as a function of the temperature difference, as shown in FIG. 4. The upper bound or the lower bound of the QC chart can be referred to as a reference relationship data.

The relationship between the intensity difference $\Delta I$ and the temperature difference $\Delta T$ of the IR camera under test can be drawn as a point or a curve. If the point or the curve (solid line in FIG. 4) is within the lower and upper bounds of the QC chart, the IR camera under test is quantitatively confirmed to be in acceptable working condition.

In practical applications, an end user will specify the compound of interest (e.g., propane as representative of the hydrocarbon class, or benzene for sensitive environmental concerns), and the manufacturer of the verification system will produce a target cell, containing the compound of interest, to meet the specifications, such as type of gas (e.g., propane or benzene), concentration (e.g., 10% of propane in nitrogen), thickness of the target cell, and pressure of the gas inside the target cell at a specified temperature. Once the specifications are set, the target cell will be produced and a verification/calibration quality control (QC) chart, which is similar to the graph (dashed lines) shown in FIG. 4, will be assigned to the specific target cell. In other words, the QC chart includes the data of the upper bound and the lower bound, as shown in FIG. 4. The distances D2 between the IR camera 500 under test and the target cell 101, and the distance D1 between the target cell 101 and the background board 106 will be specified for the QC chart to be valid. Examples of target compound may include propane, methane, and propylene.

The specifications for each target cell, including distances and QC charts, can be standardized across a group of facilities, an industrial sector, or a category of regulated industries. Standardization and consistency can then be achieved within the applicable group.

The QC charts for various compounds may be prepared in advance, and the lower bound and the upper bound for each of the QC charts for each target cell may be saved in the pixel intensity analyzer 301. The pixel intensity analyzer 301 may be electronically coupled to the cell temperature and pressure sensor 102 and the background board temperature sensor 107 to obtain the temperature information of the target cell 101 and the background board 106, respectively.

Figure 5:
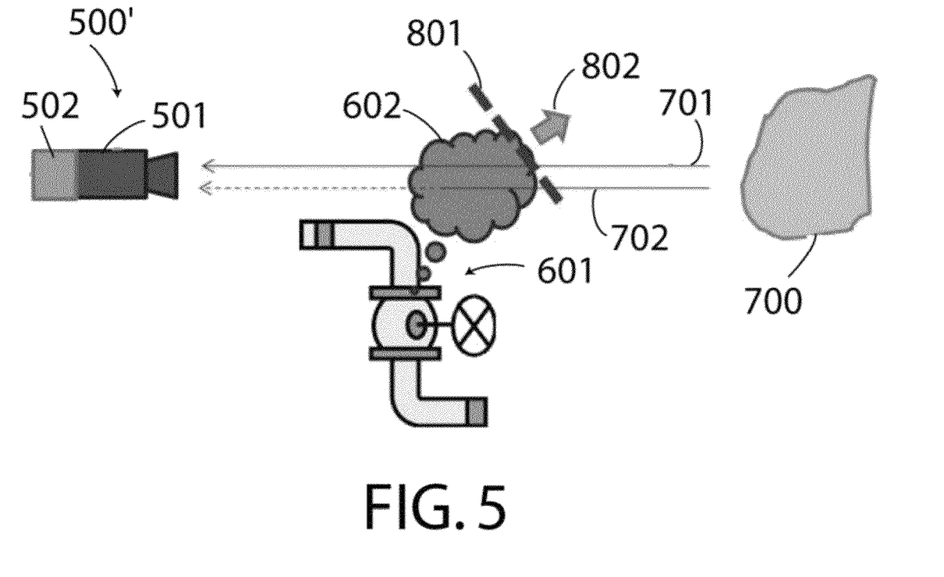
FIG. 5 shows a quantification system which can quantify the path concentration and/or hydrocarbon mass leak rate.

The quantification system 500' for quantifying the path concentration or leak rate using a plume observed by a gas imaging infrared (IR) camera is illustrated in FIG. 5. The camera 501 is a gas imaging IR camera used to capture IR images. The camera 501 includes any imaging system that is capable of detecting gas leak. The camera 501 may be an infrared imaging system, but is not limited to this type of imaging system.

Figure 6:
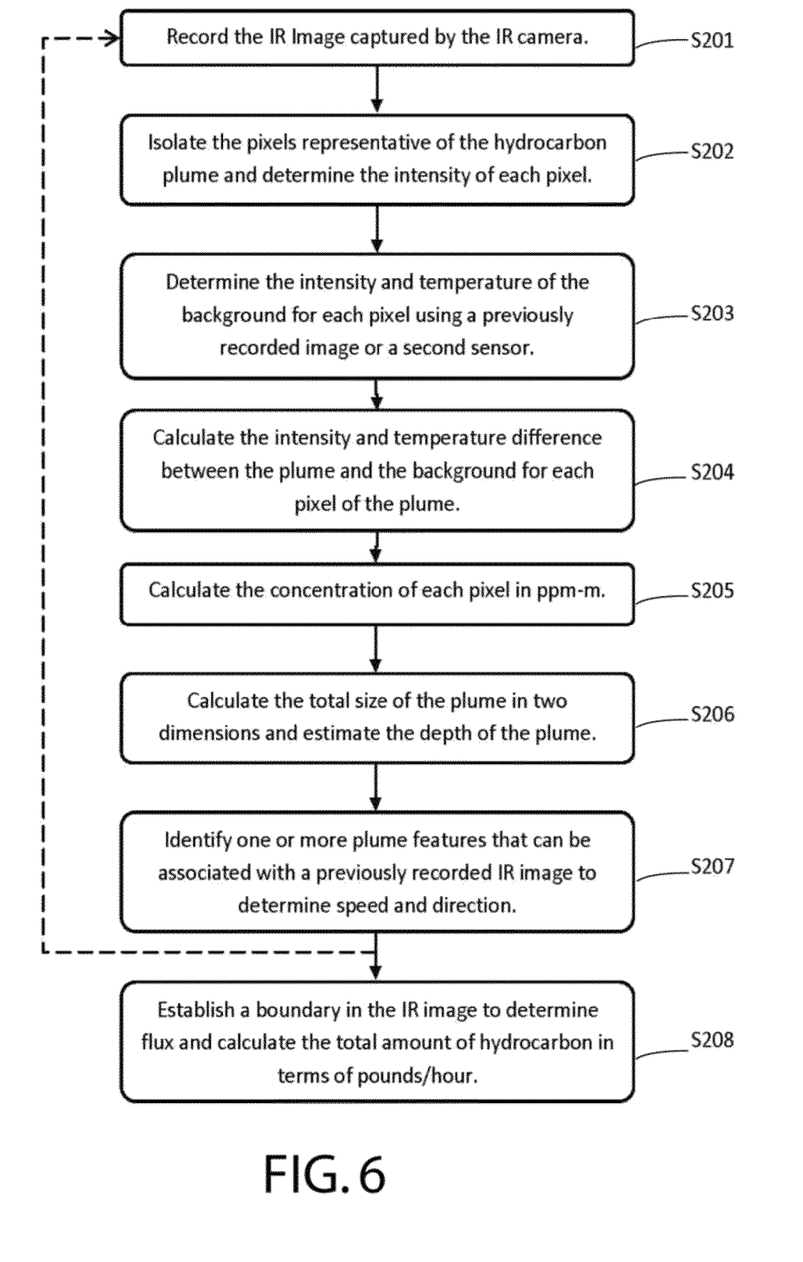
FIG. 6 shows a flowchart for performing the quantification of a hydrocarbon plume using a gas imaging camera.

Referring to FIG. 5, the quantification system 500 includes a leak quantification analyzer (LQA) 502 that is either connected to the camera 501 or embedded into the camera 502 electronic system. The LQA determines the boundaries of a hydrocarbon plume 602 resulting from a leaking process equipment component 601. Once the boundary is determined, the LQA further acquires the intensity of each pixel within the boundaries of the plume 602 based on the rays 702 that are radiated from background 700 in the scene behind the plume and attenuated by the plume. The LQA further determines the intensity of each pixel within the boundaries of the plume 602 based on the rays 701 that are also radiated from background 700 but are not attenuated by the plume. Herein, the rays 701 are referred to as unattenuated rays, and the rays 702 are referred to as attenuated rays. In one embodiment of the invention, the unattenuated rays 701 that are not attenuated by the plume 602 are acquired from a previously recorded IR image such as a previous frame from the camera 501. With the IR camera in a fixed location and a plume moving through the scene, the background intensity is determined by observing the same pixel in a previous frame when the plume is in a different location due to random wind shift. In another embodiment of the invention, the unattenuated rays 701 that are not attenuated by the plume 602 are acquired from a second IR image with spectral filtering that does not produce a response from the hydrocarbon plume. The spectral filter could be located in the cooled dewar with the sensor ("Cold filter") or in the uncooled optical path ("Warm filter"). The second IR image could be produced by the same sensor or a second sensor, but in either case the spectral filtering of the second IR image is such that the rays are not attenuated by the hydrocarbon plume and the background is observed directly. FIG. 6 shows a flowchart that illustrates the camera verification processes. The leak quantification analyzer (LQA) 502 includes a machine readable storage medium that provides instructions that cause a machine apparatus to perform operations to quantify the concentration of the hydrocarbon plume and mass leak rate. The operations are described below referring to FIG. 6.

Referring to FIG. 6, the LQA 502 records the IR image captured by the IR camera 501, preferably in the raw 14-bit data format rather than the 8-bit data format processed for display on a monitor (S201). The LQA 502 isolates the pixels representative of the hydrocarbon plume, establishes the boundary of the plume and calculates the intensity IG of each pixel within the boundary of the plume using attenuated rays 702 that are attenuated by the hydrocarbon plume (S202). The LQA determines the intensity IB and temperature Tb of the background for each pixel within the boundary of the plume (S203) using one of the embodiments described in the previous paragraph. The LQA will calculate intensity difference $\Delta I = I_G - I_B$ and temperature difference $\Delta T = Tg - Tb$ for each pixel within the boundaries of the plume (S204). The gas temperature Tg can be directly measured using a thermometer or can be estimated to be the same as ambient air temperature. The background temperature Tb may be directly measured by the IR camera 501 that has been calibrated to measure temperature in the scene at pixel level or by another remote temperature measurement device.

With the above intensity difference $\Delta I$ and $\Delta T$ acquired and calculated for each pixel within the boundary of the plume, the remaining values required to determine concentration in terms of ppm-meters are the emissivity $\epsilon(\lambda)$ of the background and the absorption coefficient $\alpha(\lambda)$ of the gas plume. The emissivity $\epsilon(\lambda)$ of the background can be determined using prior knowledge or industry standards. Similarly, the absorption coefficient $\alpha(\lambda)$ of the gas plume 602 can be determined using prior process knowledge of process gas or gas mixture and corresponding absorption coefficient from standard IR spectral library. With all necessary values directly measured or estimated, the LQA will determine the concentration for each pixel within the boundaries of the plume in terms of ppm-meters (S205).

The LQA uses the following simplified radiative transfer equation to determine the concentration of each pixel in the hydrocarbon plume:

$$I = [\epsilon(\lambda) B(T_b, \lambda) - B(T_g, \lambda)] \exp^{[-\alpha(\lambda) CL]} + B(T_g, \lambda)$$

where I represents the IR engery intensity detected by the IR camera, s represents the emissivity of the background as a function of wavelength $\lambda$, $B(T_b, \lambda)$ represents the Planck function for the background object, $B(T_g, \lambda)$ represents the Planck function for the gas plume, $\alpha(\lambda)$ represents the absorption coefficient of the gas plume, C represents the concentration of the gas plume and L represents the depth of the gas plume from the perspective of the IR camera 501. The intensity I is directly measured from the IR camera 501. The emissivity s of the background can be directly measured with an emissometer, provided from prior knowledge of the scene or estimated using an industry standard value for the facility type. To calculate the Planck function $B(T_b, \lambda)$ for the background and $B(T_g, \lambda)$ for the gas, we must know the temperature of both the background and the hydrocarbon plume. The background temperature $T_b$ can be directly measured from the IR camera 501 which has been calibrated to provide thermography measurements. The gas plume temperature $T_g$ can be directly measured with a thermocouple immersed in the plume or estimated to be equivalent to atmospheric temperature. The absorption coefficient $\alpha(\lambda)$ of the hydrocarbon plume can be provided with prior process knowledge or estimated using industry standard values. With all unknowns either directly measured or estimated, solving the RTE function for CL provides a quantitative measurement of the plume concentration at the pixel level in terms of ppm-m.

The LQA will further determine the total size of the plume in the two dimensions observable by the IR camera (S206) using factors such as the optical magnification, pixel size and distance between the IR camera and plume. The third dimension of the plume L will be estimated using various mathematical techniques allowing for a calculation of the volume of the plume. Due to the random nature of atmosphere, the plume 602 is expected to change the direction of the movement, which will result in different orientations with respect to camera 501's view angle. This will provide opportunity to measure the plume 602 at various view angles in very short period of time and to estimate three dimensions from the plume. At each view angle, the LQA will also identify one or more unique plume features to determine the speed and direction of the plume (direction 802 shown in FIG. 5) by associating these features with previous frames from the IR camera recorded by the LQA (S207). For example, atmospheric turbulence and the non-uniformity of the plume concentration will produce pockets of gas with higher concentration which appear as clusters of darker pixels. The LQA will identify the exact position of a cluster and locate a cluster in a previous frame which is of similar intensity and highly correlated to the cluster in the current frame. Once the same cluster has been identified in two (or more) frames, the LQA will determine the center of each cluster and the distance between these two centers in terms of pixels. The distance between the IR camera 501 and the gas plume 602 can be measured or provided by user input. Prior knowledge of the optical magnification and pixel density of the IR camera 501 allows the LQA to determine the absolute size (in meters) represented by a single pixel in the IR camera 501, and a conversion of the distance measurement from pixels to meters. Further, the LQA will use the frame rate of the IR camera 501 to determine the time that has elapsed between the two measurement frames and calculate the speed of the hydrocarbon plume by multiplying distance and time. Tracking a cluster of pixels from frame to frame will allow the LQA to maintain a track for each cluster and calculate the average speed and direction for the track. The LQA will determine a virtual plane 801 (shown in FIG. 5) in the IR image perpendicular to the direction of the plume movement to determine the flux of the plume as it passes the virtual plane 801 (S208). For each pixel along the boundary of the virtual plane, the LQA will determine the concentration in ppm-m. Using some knowledge of the composition of the hydrocarbon plume (or an industry standard value), dimensions of the pixel, and depth of the plume the LQA will calculate the volume of the plume within that pixel and determine the quantity of hydrocarbon (in lbs) represented by that pixel. Using established tracks of features in the hydrocarbon plume, the LQA will determine the average speed of the plume perpendicular to the virtual plane in meters per hour. The LQA will select a specific distance (in meters) perpendicular to the virtual plane and use the speed of the plume (in meters/hour) to calculate the quantity of hydrocarbon (in lbs) which passes through that distance in a given time period (hours) to determine the mass leak rate in lbs/hr.

Although practical applications of gas imaging IR cameras have spread rapidly across industries in recent years, the applications are still empirical and qualitative in nature. The outcome of a gas imaging event is based on visual interpretation by the user. There is no quantitative metric for users to judge or verify the performance of a particular IR camera. The main reason for the lack of performance metrics is that there are too many variables in an application that will influence the outcome. The method described above removes most variables and should make measurements of IR camera performance repeatable and quantifiable. This method can be used to establish a library (a cluster of the $\Delta I$ vs. $\Delta T$ charts) for various compounds under a standard set of conditions. Users can use this library as a reference.

While this invention has been described in connection with what is presently considered to be practical exemplary embodiments, it is to be understood that the invention is not limited to the disclosed embodiments, but is intended to cover various modifications and equivalent arrangements included within the scope of the claims.

What is claimed is:

1. A leak quantification system, comprising:
an analyzer coupled to a gas imaging camera that captures images of a scene which include a hydrocarbon plume of unknown concentration, the analyzer including a machine readable storage medium that provides instructions that cause a machine apparatus to perform operations to quantify a product of a concentration and a depth of the hydrocarbon plume and a mass leak rate, the operations comprising:
detecting each pixel that is included within boundaries of the hydrocarbon plume;
detecting an average intensity of attenuated rays passing through the hydrocarbon plume for said each pixel within the boundaries of the hydrocarbon plume;
detecting an average intensity of unattenuated rays, which are not attenuated by the hydrocarbon plume, for said each pixel within the boundaries of the hydrocarbon plume;
detecting a temperature of a background for said each pixel within the boundaries of the hydrocarbon plume;
acquiring a temperature of the hydrocarbon plume for said each pixel within the boundaries of the hydrocarbon plume;
calculating an intensity difference between the average intensity of the attenuated rays and the average intensity of the unattenuated rays for said each pixel within the boundaries of the hydrocarbon plume;
calculating a temperature difference between the hydrocarbon plume and the background for said each pixel within the boundaries of the hydrocarbon plume;
using a pre-established intensity difference and temperature difference chart to determine the product of the concentration and the depth of the hydrocarbon plume;
determining a size of the hydrocarbon plume using an optical magnification, a size of pixels within boundaries of the hydrocarbon plume, and a distance between the gas imaging camera and the hydrocarbon plume to directly measure two dimensions and to estimate the depth of the hydrocarbon plume;
determining a speed and a direction of the hydrocarbon plume by identifying one or more unique features of the hydrocarbon plume and associating those features with previous frames recorded by the gas imaging camera;
establishing a virtual plane perpendicular to the direction of a movement of the hydrocarbon plume to measure flux;
estimating an emissivity of the background using direct measurement or industry standard values;
estimating an absorption coefficient of a hydrocarbon molecule using industry standard values; and
determining the mass leak rate from the product of the concentration and the depth of the hydrocarbon plume, the size of the hydrocarbon plume, and the speed of the hydrocarbon plume.

2. The leak quantification system of the claim 1, comprised of the acquiring the temperature of the hydrocarbon plume including estimating the temperature of the hydrocarbon plume being the same as an ambient air temperature.

3. The leak quantification system of the claim 1, comprised of the determining the leak rate comprising:
selecting a specific virtual plane perpendicular to the direction of the movement of the hydrocarbon plume; and
calculating, from the speed of the hydrocarbon plume, a quantity of hydrocarbon which crosses the virtual plane in a given time period to determine the leak rate.

4. The leak quantification system of the claim 1, comprised of the determining the product of the concentration and the depth by using the pre-established intensity difference and temperature difference chart being including using a formula $$I = [\epsilon(\lambda) B(T_b,\lambda) - B(T_g,\lambda)] \exp^{[-\alpha(\lambda)CL]} + B(T_g,\lambda)$$

where I represents an intensity detected by the gas imaging camera, $\epsilon$ represents the emissivity of the background as a function of a wavelength $\lambda$, $B(T_b, \lambda)$ represents a Planck function for the background, $B(T_g, \lambda)$ represents a Planck function for the hydrocarbon plume, $\alpha(\lambda)$ represents the absorption coefficient of the hydrocarbon molecule, C represents the concentration of the hydrocarbon plume, and L represents the depth of the hydrocarbon plume from the perspective of the gas imaging camera.

5. The leak quantification system of the claim 1, comprised of the gas imaging camera being an infrared camera calibrated to provide thermography measurements.

6. The leak quantification system of the claim 5, comprised of the detecting the temperature of the background including directly measuring the temperature of the background by the infrared camera calibrated to provide thermography measurements.

7. A leak quantification system, comprising:
a gas imaging camera that captures images of a gas including hydrocarbon plume; and
an analyzer integrated or coupled to the gas imaging camera, the analyzer including a machine readable storage medium that provides instructions that cause a machine apparatus to perform operations to quantify a mass leak rate, the operations comprising:
detecting each pixel that is included within boundaries of the hydrocarbon plume;
detecting an intensity of attenuated rays passing through the hydrocarbon plume for said each pixel within the boundaries of the hydrocarbon plume;
detecting an intensity of unattenuated rays, which are not attenuated by the hydrocarbon plume, for said each pixel within the boundaries of the hydrocarbon plume;
detecting a temperature of a background for said each pixel within the boundaries of the hydrocarbon plume;
acquiring a temperature of the hydrocarbon plume for said each pixel within the boundaries of the hydrocarbon plume;
calculating an intensity difference between the intensity of the attenuated rays and the intensity of the unattenuated rays for said each pixel within the boundaries of the hydrocarbon plume;
calculating a temperature difference between the hydrocarbon plume and the background for said each pixel within the boundaries of the hydrocarbon plume;
estimating an emissivity of the background;
estimating an absorption coefficient of a hydrocarbon molecule;
obtaining a product of a concentration and a depth of the hydrocarbon plume from the intensity difference, the temperature difference, the emissivity of the background and the absorption coefficient of the hydrocarbon plume;
determining a two dimensional size of the hydrocarbon plume by using an optical magnification, a size of pixels within the boundaries of the hydrocarbon plume, and a distance between the gas imaging camera and the hydrocarbon plume;

determining a speed and a direction of a movement of the hydrocarbon plume by using multiple image frames of the hydrocarbon plume recorded by the gas imaging camera;

establishing a virtual plane perpendicular to the direction of the movement of the hydrocarbon plume to measure flux; and determining the mass leak rate from the product of the concentration and the depth of the hydrocarbon plume, and the speed of the movement of the hydrocarbon plume crossing the virtual plane.

8. The leak quantification system of the claim 7, comprised of the obtaining the product of the concentration and the depth of the hydrocarbon plume including using a formula:

$$I=[\epsilon(\lambda) B(T_b,\lambda)-B(T_g,\lambda)]\exp^{[-\alpha(\lambda)CL]}+B(T_g,\lambda)$$

where I represents an intensity detected by the gas imaging camera, ϵ represents the emissivity of the background as a function of a wavelength λ, B ($T_b$, λ) represents a Planck function for the background, B($T_g$,λ) represents a Planck function for the hydrocarbon plume, α(λ) represents the absorption coefficient of the hydrocarbon molecule, C represents the concentration of the hydrocarbon plume, and L represents the depth of the hydrocarbon plume from the perspective of the gas imaging camera.

9. The leak quantification system of the claim 7, comprised of the acquiring the temperature of the hydrocarbon plume including estimating the temperature of the hydrocarbon plume being the same as ambient air temperature.

10. The leak quantification system of the claim 7, comprised of the detecting the temperature of the background including directly measuring the temperature of the background by an infrared camera calibrated to provide thermography measurements.

11. The leak quantification system of the claim 7, comprised of the detecting the intensity of unattenuated rays comprising detecting the intensity of unattenuated rays from a second image with spectral filtering that does not produce a response from the hydrocarbon plume, the leak quantification system further comprising another imaging camera integrated or coupled to the analyzer, the second image being captured by said another imaging camera.

12. The leak quantification system of the claim 7, comprised of the gas imaging camera detecting the intensity of unattenuated rays.

13. The leak quantification system of the claim 7, comprised of the determining the mass leak rate comprising:

selecting a virtual plane perpendicular to the direction of the movement of the hydrocarbon plume; and calculating, from the speed of the hydrocarbon plume, a quantity of hydrocarbon which passes through the virtual plane in a given time period to determine the mass leak rate.

14. A leak quantification system, comprising:

a gas imaging camera that captures images of a gas including hydrocarbon plume; and an analyzer integrated or coupled to the gas imaging camera, the analyzer including a machine readable storage medium that provides instructions that cause a machine apparatus to perform operations to quantify a product of the concentration and the depth of hydrocarbon plume, the operations comprising:

detecting each pixel that is included within boundaries of the hydrocarbon plume;

detecting an intensity of attenuated rays passing through the hydrocarbon plume for said each pixel within the boundaries of the hydrocarbon plume;

detecting an intensity of unattenuated rays, which are not attenuated by the hydrocarbon plume, for said each pixel within the boundaries of the hydrocarbon plume;

detecting a temperature of a background for said each pixel within the boundaries of the hydrocarbon plume;

acquiring a temperature of the hydrocarbon plume for said each pixel within the boundaries of the hydrocarbon plume;

calculating an intensity difference between the intensity of the attenuated rays and the intensity of the unattenuated rays for said each pixel within the boundaries of the hydrocarbon plume;

calculating a temperature difference between the hydrocarbon plume and the background for said each pixel within the boundaries of the hydrocarbon plume;

estimating an emissivity of the background;

estimating an absorption coefficient of a hydrocarbon molecule; and obtaining a product of the concentration and the depth of the hydrocarbon plume from the intensity difference, the temperature difference, the emissivity of the background and the absorption coefficient of the hydrocarbon plume.

15. The leak quantification system of the claim 14, comprised of the obtaining the product of the concentration and the depth of the hydrocarbon plume including using a formula:

$$I=[\epsilon(\lambda) B(T_b,\lambda)-B(T_g,\lambda)]\exp^{[-\alpha(\lambda)CL]}+B(T_g,\lambda)$$

where I represents an intensity detected by the gas imaging camera, ϵ represents the emissivity of the background as a function of a wavelength λ, B ($T_b$, λ) represents a Planck function for the background, B ($T_g$, λ) represents a Planck function for the hydrocarbon plume, α(λ) represents the absorption coefficient of the hydrocarbon plume, C represents the concentration of the hydrocarbon plume, and L represents the depth of the hydrocarbon plume from the perspective of the gas imaging camera.

16. The leak quantification system of the claim 14, comprised of the acquiring the temperature of the hydrocarbon plume including estimating the temperature of the hydrocarbon plume being the same as ambient air temperature.

17. The leak quantification system of the claim 14, comprised of the detecting the temperature of the background including directly measuring the temperature of the background by an infrared camera calibrated to provide thermography measurements.

18. The leak quantification system of the claim 14, comprised of the detecting the intensity of unattenuated rays comprising detecting the intensity of unattenuated rays from a second image with spectral filtering that does not produce a response from the hydrocarbon plume, the leak quantification system further comprising another imaging camera integrated or coupled to the analyzer, the second image being captured by said another imaging camera.

19. The leak quantification system of the claim 14, comprised of the gas imaging camera detecting the intensity of unattenuated rays.

* * * * *